United States Patent [19]

Ritz et al.

[11] Patent Number: 5,496,941
[45] Date of Patent: Mar. 5, 1996

[54] PROCESS FOR CONTINUOUS PURIFICATION OF CRUDE CAPROLACTAM PREPARED FROM 6-AMINOCAPRONITRILE

[75] Inventors: Josef Ritz, Ludwigshafen; Rolf Fischer, Heidelberg; Werner Schnurr, Herxheim; Günther Achhammer, Mannheim; Hermann Luyken, Ludwigshafen; Eberhard Fuchs, Frankenthal, all of Germany

[73] Assignee: BASF Aktiengesellschaft, Ludwigshafen, Germany

[21] Appl. No.: 375,410

[22] Filed: Jan. 18, 1995

[30] Foreign Application Priority Data

Jan. 3, 1995 [DE] Germany ............. 195 00 041.2

[51] Int. Cl.⁶ ............................................. C07D 201/16
[52] U.S. Cl. ............................................. 540/540; 540/539
[58] Field of Search ........................... 540/539, 540

[56] References Cited

U.S. PATENT DOCUMENTS

| | | | |
|---|---|---|---|
| 2,301,964 | 11/1942 | Martin | 540/539 |
| 2,357,484 | 9/1944 | Martin | 540/539 |
| 2,692,878 | 10/1954 | Kahr | 540/540 |
| 2,786,052 | 3/1957 | Kampschmidt et al. | 540/540 |
| 2,828,307 | 3/1958 | Soeterbroek et al. | 540/540 |
| 3,145,198 | 8/1964 | Morbidelli et al. | 540/540 |
| 4,301,073 | 11/1981 | Fuchs et al. | 540/540 |
| 4,882,430 | 11/1989 | Neubauer et al. | 540/540 |
| 5,032,684 | 7/1991 | Neubauer et al. | 540/540 |

FOREIGN PATENT DOCUMENTS 560100  3/1944  United Kingdom ............ 540/539

Primary Examiner—Robert T. Bond
Attorney, Agent, or Firm—Keil & Weinkauf

[57] ABSTRACT

Crude capronitrile is purified by hydrogenation, subsequent treatment in an acidic medium and subsequent distillation in an alkaline medium, by a process in which (a) 6-aminocapronitrile is converted into crude caprolactam by reaction with water, (b) high boilers and low boilers are separated off from the crude caprolactam from step (a), (c) the crude caprolactam from step (b) is treated with hydrogen at from 50° to 150° C. and from 1.5 to 250 bar in the presence of a hydrogenation catalyst and, if desired, of a solvent to give a mixture A, (d1) mixture A in a solvent is passed, at from 30° to 80° C. and from 1 to 5 bar, over an ion exchanger containing terminal acid groups to give a mixture B1, or (d2) mixture A is distilled in the presence of sulfuric acid, any solvent present being removed before the addition of the sulfuric acid, to give a mixture B2, and (e) mixture B1 or mixture B2 is distilled in the presence of a base to give pure caprolactam.

2 Claims, No Drawings

PROCESS FOR CONTINUOUS PURIFICATION OF CRUDE CAPROLACTAM PREPARED FROM 6-AMINOCAPRONITRILE

The present invention relates to a process for the continuous purification of crude caprolactam by hydrogenation, subsequent treatment in an acidic medium and subsequent distillation in an alkaline medium.

It is known that caprolactam can be prepared by a Beckmann rearrangement of cyclohexanone oxime with sulfuric acid or oleum. After neutralization of the discharged rearrangement reaction mixture with ammonia, the caprolactam liberated is separated from ammonium sulfate by extraction with an organic solvent.

Depending on the method of preparation for the cyclohexanone oxime starting materials, ie. cyclohexanone and hydroxylammonium salt, and the oximation and rearrangement method, the crude caprolactam prepared by Beckmann rearrangement contains impurities which differ in type and amount. The purity of the caprolactam as a fiber raw material has to meet high requirements. A separate optimized purification process is therefore necessary for each specific process for the preparation of caprolactam from cyclohexanone oxime.

Thus, German Patent 1,253,716 discloses a process in which caprolactam is hydrogenated in the presence of hydrogenation catalysts in suspension or by the trickle-bed procedure with the addition of acids, such as sulfuric acid. In a similar process described in German Patent 1,253,715, alkali is added during the hydrogenation.

In another process described in German Patent 1,004,616, caprolactam to be purified is treated first with active carbon and then with ion exchangers and is then hydrogenated in the presence of hydrogenation catalysts in suspension or by the trickle-bed procedure, after which the hydrogenated caprolactam is treated with ion exchangers.

Furthermore, East German Patent 75,083 discloses a process for the purification of caprolactam, in which caprolactam is first distilled and then, dissolved in an organic solvent or water, is hydrogenated in the presence of a fixed-bed skeletal catalyst, after which the hydrogenated caprolactam is treated with ion exchangers. European Patent 411,455 shows that the characteristics important for the caprolactam quality, ie. the permanganate number and the content of volatile bases, can be simultaneously kept low if the crude caprolactam is hydrogenated continuously by the liquid-phase procedure.

In addition to the Beckmann rearrangement of cyctohexanone oxime to caprolactam, there are further synthesis routes leading to caprolactam: thus, it is known that 6-aminocapronitrile can be reacted with water in the gas or liquid phase, in the presence or absence of a catalyst, with liberation of ammonia to give caprolactam:

When 10–25% strength aqueous solutions of 6-aminocapronitrile are heated in the liquid phase to 250°–290° C., caprolactam is formed in a yield of up to 76% (U.S. Pat. No. 2,301,964).

Furthermore, FR-A 2,029,540 describes the cyclization of 25–35% strength 6-aminocapronitrile solutions at 220° C. in the liquid phase in water with the addition of organic solvents in the presence of, for example, zinc, copper, lead and mercury compounds. Caprolactam yields of up to 83% are obtained here.

The cyclization of 6-aminocapronitrile can also be carried out in the gas phase. Starting from 80% strength aqueous solutions, caprolactam yields of about 92% are obtained at 305° C. using alumina as a catalyst (U.S. Pat. No. 2,357,484).

6-Aminocapronitrile can also be converted into caprolactam, for example over copper/vanadium catalysts in the gas phase at 290° C. in the presence of hydrogen, water and ammonia, in a yield of about 77% (EP-A 150 295).

The 6-aminocapronitrile required for the cyclization can be prepared, for example, by partial catalytic hydrogenation of adiponitrile in the presence of ammonia as a solvent: for example, suspended catalysts, such as rhodium on magnesium oxide (U.S. Pat. No. 4,601,859), Raney nickel (U.S. Pat. No. 2,762,835, Freidlin et al., Russ. Chem. Rev. 33 (1964), WO 92/21650), nickel on alumina (U.S. Pat. No. 2 208 598) or fixed-bed catalysts, such as copper/cobalt/zinc spinels or iron/cobalt spinels (DB 848 654), cobalt on silica gel (DB 954 416, U.S. Pat. No. 2,257,814) or iron (DE 42 35 466) may be employed here.

According to WO 92/21650, aminocapronitrile yields of 60% (conversion 70%, selectivity 86%) and hexamethylenediamine yields of 9% are obtained, for example in the presence of Raney nickel. At a conversion 80%, the aminocapronitrile yield is 62% (selectivity 77%).

A purification process for crude caprolactam which was prepared from 6-aminocaprolactamwas hitherto unknown. However, since such crude caprolactam has a byproduct spectrum which differs completely from that of caprolactam prepared by a Beckmann rearrangement, it is not possible to employ the purification methods for caprolactam obtained by a Beckmann rearrangement.

Thus, crude caprolactam prepared from adiponitrile via 6-aminocapronitrile contains, for example, open-chain and cyclic nitriles, amines and imines as byproducts, which are not encountered in the crude caprolactam from the Beckmann rearrangement.

It is an object of the present invention to provide a purification process for caprolactam prepared from 6-aminocapronitrile, which process is less expensive and reliably leads to on-spec caprolactam.

We have found that this object is achieved by a process for the continuous purification of crude caprolactam by hydrogenation, subsequent treatment in an acidic medium and subsequent distillation in an alkaline medium, wherein (a) 6-aminocapronitrile is converted into crude caprolactam by reaction with water, (b) high boilers and low boilers are separated off from the crude caprolactam from step (a), (c) the crude caprolactam from step (b) is treated with hydrogen at from 50° to 150° C. and from 1.5 to 250 bar in the presence of a hydrogenation catalyst and, if desired, of a solvent to give a mixture A, (d1) mixture A in a solvent is passed, at from 30° to 80° C. and from 1 to 5 bar, over an ion exchanger containing terminal acid groups to give a mixture B1, or (d2) mixture A is distilled in the presence of sulfuric acid, any solvent present being removed before the addition of the sulfuric acid, to give a mixture B2, and (e) mixture B1 or mixture B2 is distilled in the presence of a base to give pure caprolactam.

According to the invention, 6-aminocapronitrile is reacted in the liquid or gas phase in the presence of water to give caprolactam. Processes for the cyclization of 6-aminocapronitrile are disclosed, for example, in U.S. Pat. No. 2,245,129, U.S. Pat. No. 2,301,964, EP-A 150,295 or FR-A 2 029 540, so that further information is unnecessary here.

The 6-aminocapronitrile used according to the invention as a starting material is usually obtained by hydrogenating adiponitrile by known process, for example described in DE-A 836 938, DE-A 848 654 or U.S. Pat. No. 5,151,543.

In a preferred embodiment, 6-aminocapronitrile is reacted with water in the liquid phase with the use of heterogeneous catalysts.

The reaction is carried out in the liquid phase at in general from 140° to 320° C., preferably from 160° to 280° C.; the pressure is in general from 1 to 250, preferably from 5 to 150, bar, it being necessary to ensure that the reaction mixture is predominantly liquid under the conditions used. The residence times are in general from 1 to 120, preferably from 1 to 90, in particular from 1 to 60 minutes. In some cases, residence times of from 1 to 10 minutes have proven completely sufficient.

In general, at least 0.01, preferably from 0.1 to 20, in particular from 1 to 5, mol of water are used per mol of 6-aminocapronitrile.

Advantageously, the 6-aminocapronitrile is used in the form of a 1–50, in particular 5–50, particularly preferably 5–30, % strength by weight solution in water (in which case the solvent is simultaneously a reactant), or in water/solvent mixtures. Examples of solvents are alkanols, such as methanol, ethanol, n-propanol, isopropanol, n-butanol, isobutanol and tert-butanol, and polyols, such as diethylene glycol and tetraethylene glycol, hydrocarbons, such as petroleum ether, benzene, toluene and xylene, lactams, such as pyrrolidone and caprolactam, and alkyl-substituted lactams, such as N-methylpyrrolidone, N-methylcaprolactam and N-ethylcaprolactam, and carboxylates, preferably of carboxylic acids of 1 to 8 carbon atoms. Ammonia may also be present in the reaction. Mixtures of organic solvents can of course also be used. Mixtures of water and alkanols in a water/alkanol weight ratio of 1–75/25–99, preferably 1–50/50–99, have proven particularly advantageous in some cases.

It is in principle also possible to use the 6-aminocapronitrile as a reactant and simultaneously as a solvent.

Examples of heterogeneous catalysts which may be used are: acidic, basic or amphoteric oxides of the elements of the second, third or fourth main group of the Periodic Table, such as calcium oxide, magnesium oxide, boron oxide, alumina, tin oxide or silica as pyrogenic silica, silica gel, kieselguhr, quartz or mixtures thereof, and oxides of metals of the second to sixth subgroups of the Periodic Table, such as titanium oxide, in amorphous form or as anatase or rutile, zirconium oxide, zinc oxide, manganese oxide or mixtures thereof. Oxides of the lanthanides and actinides, such as cerium oxide, thorium oxide, praseodymium oxide, samarium oxide, rare earth mixed oxides or mixtures thereof with above-mentioned oxides may also be used. Examples of further catalysts may be:

Vanadium oxide, niobium oxide, iron oxide, chromium oxide, molybdenum oxide, tungsten oxide or mixtures thereof. Mixtures of the stated oxides with one another are also possible. Some sulfides, selenides and tellurides, such as zinc telluride, tin selenide, molybdenum sulfide, tungsten sulfide and sulfides of nickel, of zinc and of chromium, may also be employed.

The abovementioned compounds may be doped with compounds of the first and seventh main groups of the Periodic Table or may contain said compounds.

Zeolites, phosphates and heteropolyacids as well as acidic and alkaline ion exchangers, for example Naphion®, are further examples of suitable catalysts.

If necessary, these catalysts may contain up to 50% by weight in each case of copper, tin, zinc, manganese, iron, cobalt, nickel, ruthenium, palladium, platinum, silver or rhodium.

The catalysts may be used in the form of unsupported or supported catalysts, depending on the composition of the catalyst. For example, titanium dioxide may be used as titanium dioxide extrudates or as titanium dioxide applied in a thin layer on a carrier. All methods described in the literature may be used for applying titanium dioxide to a carrier, such as silica, alumina or zirconium dioxide. Thus, a thin titanium dioxide layer may be applied by hydrolysis of titanium organyls, such as titanium isopropylate or titanium butylate, or by hydrolysis of $TiCl_4$ or other inorganic titanium-containing compounds. Titanium dioxide-containing sols may also be used.

Further suitable compounds are zirconyl chloride, aluminum nitrate and cerium nitrate.

Suitable carriers are powders, extrudates or pellets of the stated oxides themselves or of other stable oxides, such as silica. The carriers used may be rendered macroporous in order to improve the mass transport.

In a further preferred embodiment, 6-aminocapronitrile is cyclized in the liquid phase with water at elevated temperatures in the absence of a catalyst by heating an aqueous solution of 6-aminocapronitrile in the liquid phase in a reactor without the addition of a catalyst to give a mixture I consisting essentially of water, caprolactam and a high-boiling fraction (high boilers). In this preferred embodiment, water is preferably used in excess; particularly preferably from 10 to 150, in particular from 20 to 100, mol of water are used per mol of 6-aminocapronitrile, an aqueous solution of 6-aminocapronitrile being obtained. In a further preferred embodiment, from 5 to 25 mol of water are usually used per mol of 6-aminocapronitrile, and the solution can be further diluted to 5–25% by weight of 6-aminocapronitrile, in general by adding an organic solvent.

Examples of suitable solvents are:

$C_1$–$C_4$-alkanols, such as methanol, ethanol, n-propanol, isopropanol and butanols, glycols, such as ethylene glycol, diethylene glycol, triethylene glycol and tetraethylene glycol, ethers, such as methyl tert-butyl ether and diethylene glycol diethyl ether, $C_6$–$C_{10}$-alkanes, such as n-hexane, n-heptane, n-octane, n-nonane and n-decane, and cyclohexane, benzene, toluene, xylene, lactams, such as pyrrolidone, caprolactam and N-$C_1$–$C_4$-alkyllagtams, such as N-methylpyrrolidone, N-methylcaprolactam and N-ethylcaprolactam.

In a preferred embodiment, from 0 to 5, preferably from 0.1 to 2, % by weight of ammonia, hydrogen or nitrogen may be added to the reaction mixture.

The reaction is preferably carried out at from 200° to 370° C., preferably from 220° to 350° C., particularly preferably from 240° to 320° C.

The reaction is usually carried out under superatmospheric pressure, the pressure being chosen as a rule in the range from 0.1 to 50, preferably from 5 to 25 MPa, so that the reaction mixture is preferably present as the liquid phase.

The reaction time depends essentially on the process parameters chosen and is in general from 20 to 180, preferably from 20 to 90, minutes in the continuous process. As a rule, the conversion decreases in the case of shorter reaction times, and observations to date have shown that longer reaction times result in the formation of troublesome oligomers.

The cyclization is preferably carried out continuously, preferably in a tube reactor, a stirred kettle or a combination thereof.

The cyclization can also be carried out batchwise. The reaction time in this case is usually from 30 to 180 minutes.

As a rule, the discharge mixture consists essentially of from 50 to 98, preferably from 80 to 95, % by weight of water and from 2 to 50, preferably from 5 to 20, % by weight of a mixture consisting essentially of from 50 to 90, preferably from 65 to 85, % by weight of caprolactam and from 10 to 50, preferably from 15 to 35, % by weight of a high-boiling fraction (high boilers).

In step (b) of the novel process, high boilers and low boilers are removed from the crude caprolactam obtained in step (a), by separating ammonia, any solvent present, such as those mentioned above, in particular alcohols, excess water and unconverted 6-aminocapronitrile and any low-boiling byproducts from crude caprolactam by distillation, preferably via the top, and then separating crude caprolactam from high boilers, such as oligomers of 6-aminocaproic acid, by distillation, preferably via the top. Observations to date have shown that whether the low boilers are separated off before the high boilers or the latter before the former or the two are separated off simultaneously is not critical for the success of the invention.

According to the invention, the crude caprolactam prepurified in step (b) is treated with hydrogen, the crude caprolactam being used in the form of a melt, preferably dissolved in a solvent.

Preferred solvents are those which are inert under the conditions of the hydrogenation and of the treatment with an ion exchanger. The following are particularly suitable: $C_1$–$C_3$-alkanols, such as methanol, ethanol, n-propanol and isopropanol, preferably ethanol, and particularly preferably water.

In a preferred embodiment, the solvent used is that from the cyclization of the 6-aminocapronitrile, provided that an alcohol or water was used there.

From 50 to 95, preferably from 70 to 95, % by weight solutions of crude caprolactam are usually used in the hydrogenation, the percentages being based on the solution. When the solvent from the cyclization step is employed, it may be necessary to add solvent or distill off solvent in order to reach the desired concentration.

According to the invention, the treatment with hydrogen is carried out at from 50° to 150° C., preferably from 60° to 95° C., particularly preferably from 70° to 90° C., in the liquid phase. The pressure is chosen as a function of the temperature, so that a liquid phase is maintained. According to the invention, the pressure is from 1.5 to 250, preferably from 5 to 100, particularly preferably from 5 to 20, bar.

In general, hydrogen is used in amounts of from 0.0001 to 5.0, preferably from 0.001 to 0.7, particularly preferably from 0.03 to 0.3 mol, per mol of caprolactam.

The residence time is as a rule from 10 to 300, preferably from 15 to 200, minutes.

The catalyst space velocity is usually chosen in the range from 1 to 6, preferably from 1.5 to 4, kg of caprolactam per liter of catalyst per hour.

The hydrogenation can be carried out either in suspension or in a fixed bed, in the latter case a caprolactam solution preferably being passed together with hydrogen, upward or downward, over a fixed-bed catalyst in a tubular zone.

Observations to date have shown that hydrogenation catalysts which may be used are preferably those which are based on a metal selected from the group consisting of iron, nickel, cobalt, ruthenium, rhodium, palladium, osmium, iridium and platinum, particularly preferably cobalt, nickel and palladium, very particularly preferably palladium, in the form of unsupported catalysts or supported catalysts, preferably the latter.

In a preferred embodiment, supported palladium catalysts which contain from 0.01 to 10, preferably from 0.05 to 5, particularly preferably from 0.1 to 2, % by weight, based on the catalyst, of palladium are used. Preferably used carriers are active carbon, alumina, zinc oxide, silica, titanium dioxide, lanthanum oxide or zirconium dioxide or mixtures thereof.

In a further preferred embodiment, supported nickel catalysts which contain from 1 to 80, preferably from 5 to 50, % by weight, based on the catalyst, of nickel are used. Furthermore, the supported nickel catalyst may contain activating additives based on the elements of zirconium, manganese, copper or chromium, these additives being present, in general in oxide form, in amounts of from 0.1 to 20, preferably from 1 to 5, % by weight, based on the amount of nickel used.

Preferably used carriers are aluminum oxide, silica gel, aluminas, active carbon, magnesium silicates, aluminum phosphate and boron phosphate, particularly preferably magnesium silicates, aluminum phosphate, boron phosphate and aluminum oxide.

The preparation of such precipitated or impregnated catalysts is described, for example, in Ullmann's Encyclopedia of Industrial Chemistry, volume A5, pages 348–350, fifth completely revised edition.

In a further preferred embodiment, supported catalyst in which the catalytically active metals are concentrated at the surface are used. Such catalysts are generally obtained by methods known per se, by treating pre-shaped carriers comprising the abovementioned substances in the form of pellets, beads or extrudates with an aqueous solution of the metal salts, for example of the nitrates, drying them, calcining them and then activating them with hydrogen.

In a preferred embodiment, supported palladium or nickel catalysts are arranged so that they are fixed, for example in the form of a bed, in a tubular zone, for example having a ratio of length to diameter of from 10:1 to 50:1, and the (crude) caprolactam solution and hydrogen are passed over the fixed-bed catalyst by the liquid phase or trickle-bed procedure.

Observations to date have shown that particularly the UV index and the permanganate titration number (PTN) of the crude caprolactam improve as a result of the treatment with hydrogen.

Cooling and letting down the pressure gives a mixture A which essentially consists of caprolactam and solvent, where one is used. If the hydrogenation is carried out in a caprolactammelt, the discharged hydrogenation mixture is generally dissolved in one of the solvents stated above for the hydrogenation, preferably water, before the treatment with ion exchanger.

According to the invention, mixture A in a solvent is passed, in step (d1), at from 30° to 80° C., preferably from 50° to 60° C., and at from 1 to 5, preferably from 1 to 2 bar, over an ion exchanger which contains terminal acid groups to give a mixture B1, which is discharged.

The ion exchangers used are preferably highly acidic, ie. sulfocontaining, ion exchangers in the H form. Suitable ion exchangers are commercially available, for example as Amberlite®, Dowex® or Lewatit® (cf. for example Ullmann's Encyclopedia of Industrial Chemistry, volume A14, fifth completely revised edition, page 451).

The loading of the ion exchanger is chosen as a rule in the range from 1 to 15, preferably from 1 to 10, kg of caprolactam per l of ion exchanger per hour.

Observations to date have shown that the UV index is further improved as a result of the treatment with the cationic exchanger.

The laden ion exchanger can usually be regenerated by washing with an aqueous mineral acid, such as sulfuric acid or phosphoric acid, and the basic compounds fixed on the ion exchanger can generally be removed as aqueous solutions of the corresponding salts.

According to the invention, the treatment with the ion exchanger can be replaced by a distillation in the presence of sulfuric acid (step (d2)), any solvent present being removed before the addition of the sulfuric acid.

In a preferred embodiment, any solvent present is removed in a distillation column having from two to four, particularly preferably two or three, theoretical plates, at a bottom temperature of not more than 145° C. The pressure is chosen as a function of the selected temperature. Usually, the pressure is chosen in the range from 35 to 65, preferably from 40 to 60, mbar (measured at the top of the distillation column) when the bottom temperature is 145° C.

According to the invention, sulfuric acid, in general from 0.1 to 0.5, preferably from 0.2 to 0.3, % by weight, based on the amount of caprolactam, of sulfuric acid (calculated as 100% strength by weight sulfuric acid) is added to the crude caprolactam thus obtained or the crude caprolactam which is already solvent-free.

Distillation is then carried out to give a mixture B2, and the distillation residue containing sulfuric acid is advantageously fed to a cleavage plant for sulfuric acid. In a preferred embodiment, distillation is effected in a distillation column having from 12 to 18, preferably from 14 to 16, theoretical plates, at a top pressure of from 3 to 6, preferably from 3 to 4, mbar and a bottom temperature of not more than 145° C.

The mixture B1 or B2 obtained in the treatment in the acidic medium, either by treatment with an ion exchanger or by treatment with sulfuric acid, is distilled, according to the invention (step e) in the presence of a base. Alkali metal or alkaline earth metal compounds, such as hydroxides or water-soluble carbonates, eg. lithium hydroxide, sodium hydroxide, potassium hydroxide, magnesium hydroxide, calcium hydroxide, sodium carbonate or mixtures thereof, particularly preferably sodium hydroxide in the form of sodium hydroxide solution, are usually used as the base.

The amount of added base is chosen as a rule in the range from 0.05 to 0.9, preferably from 0.1 to 0.8, mol%, based on caprolactam. In a preferred embodiment, from 0.05 to 0.25, preferably from 0.1 to 0.15, % by weight of sodium hydroxide solution (calculated as 100% strength by weight) is used.

The distillation can be carried out in a manner known per se, solvent, low boilers and high boilers being separated off from caprolactam.

In a preferred embodiment, the solvent, in particular water, is first distilled off via the top from the mixture B1 or B2 to which a base has been added, as a rule in a distillation column, a bottom temperature of not more than 140° C. being chosen and the pressure correspondingly adjusted. A pressure of from 35 to 65, preferably from 40 to 60, mbar (measured at the top of the distillation column) is preferably employed. The bottom product is advantageously fed to a second distillation column.

The bottom product of the first distillation column is distilled in general in a further distillation column, as a rule at from 4 to 6, preferably 4, mbar (measured at the top of the column) and at a bottom temperature of not more than 145° C. In this distillation stage, low boilers are usually removed. The bottom product is preferably fed to a third distillation column.

The bottom product of the second distillation column is fed as a rule to a further distillation column, a pressure of from 4 to 6, preferably 4, mbar and a bottom temperature of not more than 145° C., usually being employed. Observations to date have shown that the top product consists of on-spec pure caprolactam.

In a further preferred embodiment, the bottom product of the third column can be fed to a falling-film evaporator, it being possible to separate off further caprolactam, which is advantageously recycled to the first distillation column.

The variant in which sodium hydroxide solution is used as the base is also preferred. Here, the sodium-containing bottom product of the third column or of the falling-film evaporator can be fed to an incineration plant, sodium carbonate and steam being obtained.

It is also possible to combine the separation operations of the second and third columns into a single operation by using only one distillation column. In this case, the low boilers are usually separated off by the top, the high boilers by the bottom and caprolactam via a side stream. A bleed stream of the low boilers is advantageously recycled to step (c) (treatment with hydrogen).

Observations to date have shown that the UV index is further reduced as a result of the working up by distillation in the presence of a base.

The sequence of purification steps comprising hydrogenation, treatment in an acidic medium and distillation in the presence of a base makes it possible, in the novel process, to prepare a pure lactam which completely fulfills the specifications of pure caprolactam obtained by Beckmann rearrangement in terms of the characteristics permanganate absorbence number (PAN), permanganate titration number (PTN), free bases, volatile bases (VB) and UV index (UV). The content of impurities detectable by gas chromatography is as a rule from 100 to 150 ppm, based on caprolactam. Since some impurities in the region of 10 ppm or less may make it impossible to adhere to the characteristics, and the structure of many impurities in an amount of 10 ppm or less and their chemical behavior in purification steps are not known, the success of the novel process was not foreseeable.

EXAMPLE

The purification sequence was carried out using crude caprolactam which was obtained by cyclization of a 10% strength ethanolic 6-aminocapronitrile (ACN) solution in the presence of two moles of water per mol of ACN:

A solution of 6-aminocapronitrile (ACN) in water and ethanol (10% by weight of ACN, 6.4% by weight of water, remainder ethanol) was passed, at 100 bar, into a heated tube reactor having a capacity of 25 ml (diameter 6 mm, length 800 mm) and filled with titanium dioxide (anatase) in the form of 1.5 mm extrudates, the reaction temperature being 240° C. and the residence time 30 minutes. The product stream leaving the reactor was analyzed by gas chromatography and high pressure liquid chromatography (HPLC). Conversion: 100%, yield: 88%.

The reacted mixture was freed from high boilers and low boilers by fractional distillation. The crude caprolactam thus obtained had a purity of 99.5% according to gas chromatographic analysis.

1000 g of the crude caprolactam were dissolved in 250 g of water. 3.5 g of 5% strength by weight palladium on active carbon as carrier were added to the aqueous solution in an autoclave, and the stirred mixture was hydrogenated for four hours at 80° C./5 bar.

After the autoclave had been cooled and let down, the catalyst was filtered off. The filtrate was passed over 1 l of a highly acidic ion exchanger (Amberlite® IR 120, H form) at 50° C. and atmospheric pressure in the course of 0.6 hour by the trickle-bed procedure.

4 g of a 25% strength aqueous sodium hydroxide solution were added to the discharge from the ion exchanger. The water was distilled off in a distillation column having 2 theoretical plates, at a top pressure of 50 mbar and a bottom temperature of 135° C.

The low boilers were distilled off from the bottom product of the first column in a second column having 15 theoretical plates, at a top pressure of 3.5 mbar and a bottom temperature of 140° C.

The bottom product of the second column was distilled in a third column having 15 theoretical plates. At a top pressure of 4 mbar and a bottom temperature of 145° C., a total of 990 g of caprolactam were distilled via the top (99%, based on crude caprolactam used).

According to gas chromatographic analysis, the resulting pure caprolactam contained altogether only 140 ppm of impurities, and compounds which could adversely affect the polymerization of caprolactam to nylon 6 were not found. The characteristics of the pure lactam were:

| | |
|---|---|
| PAN: | 1.5 |
| PTN: | 1.2 |
| Free bases: | <0.05 meq/kg |
| Volatile bases: | <0.5 meq/kg |
| UV: | 2.5 |

The caprolactam prepared from 6-aminocapronitrile thus fulfills the specifications required for Beckmann caprolactam.

The improvement in UV index and permanganate titration number (PTN) by the individual purification steps is demonstrated in Table 1.

TABLE 1

| Sample | UV index | Permanganate titration number (PTN) |
|---|---|---|
| Discharged cyclization mixture | 110 | 400 |
| Discharged hydrogenation mixture | 40 | 390 |
| Discharge from ion exchanger | 15 | not measured |
| Pure lactam after NaOH distillation | 2.5 | 1.2 |

Permanganate Titration Number (PTN)

The stability of caprolactam to potassium permanganate was determined titrimetrically. The permanganate titration number (PTN) corresponded to the consumption of 0.1N potassium permanganate solution in ml, based on 1 kg of caprolactam, which was found in the titration of a solution containing sulfuric acid.

Permanganate Absorbence Number (PAN)

The stability of caprolactam to potassium permanganate was determined photometrically (cf. also ISO method 8660). For this purpose, equal amounts of 0.01N potassium permanganate solution were added to 3% (m/m) aqueous caprolactam solution and to a blank sample (distilled water). After 10 minutes, the absorbences E at 420 nm of both the caprolactam sample and the blank sample were compared. The permanganate absorbence number was calculated from the measured absorbence as $$(E - E_0)_{420} \cdot \frac{100}{3}.$$

Volatile Bases (VB)

(Determination in a Parnas apparatus; cf. also ISO method 8661 Caprolactam for industrial use—Determination of volatile bases content)

In a distillation in an alkaline medium, the volatile bases were liberated from the sample (Kjeldahl apparatus), taken up in 0.01N hydrochloric acid and determined by titration with 0.01N sodium hydroxide solution, the weight of the caprolactam sample being 20±0.1 g.

$$VB = \frac{(B - A) \times 0{,}01}{20} \times 1000 \text{ meq/kg}$$

A=consumption of 0.01N sodium hydroxide solution
B=consumption of 0.01N sodium hydroxide solution for a blank determination UV Index (UV)

The particular absorbences of a 50% (m/m) aqueous caprolactam solution at 270, 280, 290, 300, 310, 320, 330, 340, 350 and 360 nm were determined in a 10 cm cell. The sum of the absorbences was multiplied by 2 and gave the UV index, based on 100% caprolactam.

Free Bases

In order to determine the free bases, 150 ml of distilled CO2-free water gassed with nitrogen was brought to exactly pH 7.0 with 0.01N sodium hydroxide solution, and 50+/−0.1 g of caprolactam were added. Preparation was then carried out at 25° C. with 0.01N hydrochloric acid to pH 7.0. The amount of free base could then be calculated using the following formula, where A (ml) is the consumption of 0.01N hydrochloric acid:

Free bases=0.01 * A * 1000/50=0.2 * A meq/kg

We claim:
1. A process for the continuous purification of crude caprolactam by hydrogenation, subsequent treatment in acidic medium and subsequent distillation in an alkaline medium, wherein
   (a) 6-aminocapronitrile is converted into crude caprolactam by reaction with water,
   (b) high boilers and low boilers are separated off from the crude caprolactam from step (a),
   (c) the crude caprolactam from step (b) is treated with hydrogen at from 50° to 150° C. and from 1.5 to 250 bar in the presence of a hydrogenation catalyst and, if desired, of a solvent to give a mixture A,
   (d1) mixture A in a solvent is passed, at from 30° to 80° C. and from 1 to 5 bar, over an ion exchanger containing terminal acid groups to give a mixture B1, or
   (d2) mixture A is distilled in the presence of sulfuric acid, any solvent present being removed before the addition of the sulfuric acid, to give a mixture B2, and
   (e) mixture B1 or mixture B2 is distilled in the presence of a base to give pure caprolactam.
2. The process of claim 1, wherein the solvent is water.

\* \* \* \* \*